US011083600B2

(12) United States Patent
Gill

(10) Patent No.: US 11,083,600 B2
(45) Date of Patent: Aug. 10, 2021

(54) PROSTHETIC DIGIT FOR USE WITH TOUCHSCREEN DEVICES

(71) Applicant: TOUCH BIONICS LIMITED, Livingston (GB)

(72) Inventor: Hugh Gill, Paisley Strathclyde (GB)

(73) Assignee: Touch Bionics Limited, Livingston (GB)

( * ) Notice: Subject to any disclaimer, the term of this patent is extended or adjusted under 35 U.S.C. 154(b) by 92 days.

(21) Appl. No.: 16/011,108

(22) Filed: Jun. 18, 2018

(65) Prior Publication Data

US 2018/0296368 A1 Oct. 18, 2018

Related U.S. Application Data

(62) Division of application No. 15/120,784, filed as application No. PCT/GB2015/050337 on Feb. 6, 2015, now Pat. No. 9,999,522.

(30) Foreign Application Priority Data

Feb. 25, 2014 (GB) ..................................... 1403265

(51) Int. Cl.
*A61F 2/54* (2006.01)
*G06F 3/041* (2006.01)
(Continued)

(52) U.S. Cl.
CPC ................ *A61F 2/586* (2013.01); *A61F 2/70* (2013.01); *G06F 3/0416* (2013.01);
(Continued)

(58) Field of Classification Search
CPC .... A61F 2/586; A61F 2/68; A61F 2/70; A61F 2002/5038; A61F 2240/001; A61F 2002/701; A61F 2002/5072; G06F 3/0416
(Continued)

(56) References Cited

U.S. PATENT DOCUMENTS

| | | | |
|---|---|---|---|
| 760,102 | A | 5/1904 | Carnes |
| 1,253,823 | A | 1/1918 | Hobbs |

(Continued)

FOREIGN PATENT DOCUMENTS

| | | |
|---|---|---|
| CN | 1803413 | 7/2006 |
| CN | 204274727 | 4/2015 |

(Continued)

OTHER PUBLICATIONS

International Search Report and Written Opinion in Application No. PCT/GB2015/050337, dated Apr. 29, 2015.

(Continued)

*Primary Examiner* — Peter Dungba Vo
*Assistant Examiner* — Kaying Kue
(74) *Attorney, Agent, or Firm* — Knobbe, Martens, Olson & Bear, LLP

(57) ABSTRACT

A digit for a prosthetic hand is provided. The digit has a base member (12) attachable to the hand and at least one digit member (18) pivotably connected to the base member. The at least one digit member (18) has a digit tip (22) remote from the base member (12), and the digit member is at least partially covered with at least one conductive substance (26,40) which defines a conductive path which leads from the digit tip towards the base member. A method of manufacturing such a digit is also provided.

18 Claims, 2 Drawing Sheets

(51) Int. Cl.
*A61F 2/58* (2006.01)
*A61F 2/70* (2006.01)
*A61F 2/50* (2006.01)

(52) U.S. Cl.
CPC ................. *A61F 2002/5038* (2013.01); *A61F 2002/5072* (2013.01); *A61F 2002/701* (2013.01); *A61F 2240/001* (2013.01)

(58) Field of Classification Search
USPC ................ 29/428, 525.01, 592.1, 434, 281.5
See application file for complete search history.

(56) References Cited

U.S. PATENT DOCUMENTS 1,507,682 A 9/1924 Pecorella et al.
1,507,683 A 9/1924 Pecorella et al.
2,445,711 A * 7/1948 Fitch ......................... A61F 2/58 623/58
2,477,463 A * 7/1949 Otterman ................ A61F 2/582 623/60
2,482,555 A 9/1949 Otterman
2,508,156 A 5/1950 Gillman
2,516,791 A 7/1950 Motis et al.
2,549,716 A 4/1951 Simpson
2,586,293 A 2/1952 Birkigt
2,592,842 A * 4/1952 Alderson .................. A61F 2/54 623/58
2,669,727 A 2/1954 Opuszenski
2,983,162 A 5/1961 Musser
3,406,584 A 10/1968 Roantree
3,509,583 A 5/1970 Fraioli
3,582,857 A 6/1971 Kishel
3,641,832 A 2/1972 Shigeta et al.
3,683,423 A 8/1972 Crapanzano
3,751,995 A 8/1973 Carlson
3,837,010 A 9/1974 Prout
3,866,246 A 2/1975 Seamone et al.
3,883,900 A 5/1975 Jerard et al.
3,922,930 A 12/1975 Fletcher et al.
4,030,141 A 6/1977 Graupe
4,044,274 A 8/1977 Ohm
4,084,267 A 4/1978 Zadina
4,094,016 A 6/1978 Eroyan
4,114,464 A 9/1978 Schubert et al.
4,197,592 A 4/1980 Klein
4,398,110 A 8/1983 Flinchbaugh et al.
4,558,704 A 12/1985 Petrofsky
4,577,127 A 3/1986 Ferree et al.
4,623,354 A 11/1986 Childress et al.
4,678,952 A 7/1987 Peterson et al.
4,808,187 A 2/1989 Patterson et al.
4,813,303 A 3/1989 Beezer et al.
4,822,238 A 4/1989 Kwech
4,955,918 A 9/1990 Lee
4,960,425 A 10/1990 Yan et al.
4,990,162 A 2/1991 LeBlanc et al.
5,020,162 A 6/1991 Kersten et al.
5,062,673 A 11/1991 Mimura
5,088,125 A 2/1992 Ansell et al.
5,133,775 A 7/1992 Chen
5,246,463 A 9/1993 Giampapa
5,252,102 A 10/1993 Singer et al.
5,387,245 A 2/1995 Fay et al.
5,413,611 A 5/1995 Haslam, II et al.
5,498,472 A 3/1996 Gold
5,501,498 A 3/1996 Ulrich
5,581,166 A 12/1996 Eismann et al.
5,605,071 A 2/1997 Buchanan, Jr.
5,785,960 A 7/1998 Rigg et al.
5,851,194 A 12/1998 Fratrick
5,852,675 A 12/1998 Matsuo et al.
5,888,213 A 3/1999 Sears et al.
5,888,246 A 3/1999 Gow
6,111,973 A 8/2000 Holt et al.
6,175,962 B1 1/2001 Michelson
6,223,615 B1 5/2001 Huck
6,244,873 B1 6/2001 Hill et al.
6,344,062 B1 2/2002 Abboudi et al.
6,361,570 B1 3/2002 Gow
6,517,132 B2 2/2003 Matsuda et al.
6,591,707 B2 7/2003 Torii et al.
6,660,043 B2 12/2003 Kajitani et al.
6,786,112 B2 9/2004 Ruttor
6,896,704 B1 5/2005 Higuchi et al.
6,908,489 B2 6/2005 Didrick
6,918,622 B2 7/2005 Kim et al.
7,144,430 B2 12/2006 Archer et al.
7,243,569 B2 7/2007 Takahashi et al.
7,316,304 B2 1/2008 Heravi et al.
7,316,795 B1 1/2008 Knauss
7,370,896 B2 5/2008 Anderson et al.
7,481,782 B2 1/2009 Scott et al.
7,640,680 B1 1/2010 Castro
7,655,051 B2 2/2010 Stark
7,823,475 B2 11/2010 Hirabayashi et al.
7,867,287 B2 1/2011 Puchhammer
7,922,773 B1 * 4/2011 Kuiken ..................... A61F 2/60 623/24
8,016,893 B2 9/2011 Weinberg et al.
8,052,185 B2 11/2011 Madhani
8,100,986 B2 1/2012 Puchhammer et al.
8,197,554 B2 6/2012 Whiteley et al.
8,257,446 B2 9/2012 Puchhammer
8,337,568 B2 12/2012 Macduff
8,343,234 B2 1/2013 Puchhammer
8,491,666 B2 7/2013 Schulz
8,579,991 B2 11/2013 Puchhammer
8,593,255 B2 11/2013 Pang et al.
8,657,887 B2 2/2014 Gill
8,662,552 B2 3/2014 Torres-Jara
8,663,339 B2 3/2014 Inschlag et al.
8,690,963 B2 4/2014 Puchhammer
8,696,763 B2 4/2014 Gill
8,739,315 B2 * 6/2014 Baacke ................... G06F 3/014 2/163
8,747,486 B2 6/2014 Kawasaki et al.
8,795,387 B1 8/2014 Razink
8,803,844 B1 * 8/2014 Green ................... G06F 3/0445 345/174
8,808,397 B2 8/2014 Gow
8,828,096 B2 9/2014 Gill
8,900,327 B2 12/2014 Bertels et al.
8,915,528 B2 12/2014 Haslinger
8,951,303 B2 2/2015 Dehoff et al.
8,979,943 B2 3/2015 Evans et al.
8,984,736 B2 3/2015 Radocy
8,986,395 B2 3/2015 McLeary
8,995,760 B2 3/2015 Gill
8,999,003 B2 4/2015 Wenstrand et al.
9,016,744 B2 4/2015 Starkey
9,017,422 B2 4/2015 Locker
9,039,057 B2 5/2015 Schvalb et al.
9,071,170 B2 6/2015 Baba et al.
9,072,614 B2 7/2015 Starkey et al.
9,072,616 B2 7/2015 Schulz
9,114,028 B2 8/2015 Langenfeld et al.
9,278,012 B2 3/2016 Gill
9,320,621 B2 4/2016 Iversen et al.
9,333,096 B2 5/2016 Perez de Alderete et al.
9,364,364 B2 6/2016 Williams
9,370,430 B2 6/2016 MacDuff
9,375,319 B2 6/2016 MacDuff
9,375,325 B2 6/2016 Garrec et al.
9,381,099 B2 7/2016 Perry et al.
9,387,095 B2 * 7/2016 McLeary ................ A61F 2/586
9,402,749 B2 * 8/2016 Gill ......................... A61F 2/586
9,435,400 B2 9/2016 Cheung et al.
9,456,909 B2 10/2016 Johnson et al.
9,463,085 B1 10/2016 Theobald
9,463,100 B2 10/2016 Gill
9,468,540 B2 10/2016 Nagatsuka et al.
9,474,630 B2 10/2016 Veatch
9,474,631 B2 10/2016 Veatch

(56) References Cited

U.S. PATENT DOCUMENTS 9,510,958 B2 12/2016 Mori
9,579,218 B2 2/2017 Lipsey et al.
9,579,219 B2 2/2017 Amend, Jr. et al.
9,585,771 B2 3/2017 Baba et al.
9,592,134 B2 3/2017 Varley
9,629,731 B2 4/2017 Thompson, Jr. et al.
9,636,270 B2 5/2017 Miyazawa
9,707,103 B2 * 7/2017 Thompson, Jr. ........ A61F 2/586
9,720,515 B2 8/2017 Wagner et al.
9,730,813 B2 8/2017 Evans et al.
9,737,418 B2 8/2017 Veatch
9,744,055 B2 8/2017 Engeberg et al.
9,814,604 B2 11/2017 Jury
9,839,534 B2 12/2017 Lipsey et al.
9,861,499 B2 1/2018 Sensinger
9,877,848 B2 1/2018 Ikebe
9,889,059 B2 2/2018 Arakawa
9,913,737 B2 3/2018 Hunter
9,931,229 B2 4/2018 Veatch
9,974,667 B1 5/2018 Cazenave
9,999,522 B2 6/2018 Gill
10,004,611 B2 6/2018 Iversen et al.
10,004,612 B2 6/2018 Iversen et al.
10,022,248 B2 7/2018 Thompson, Jr. et al.
10,028,880 B2 7/2018 Arata et al.
10,034,780 B2 7/2018 Lipsey et al.
10,045,865 B2 8/2018 Veatch
10,045,866 B2 8/2018 Armbruster
10,052,216 B2 8/2018 Moyer et al.
10,076,425 B2 9/2018 Farina et al.
10,092,423 B2 10/2018 Goldfarb et al.
10,265,197 B2 4/2019 Gill et al.
10,318,863 B2 6/2019 Lock et al.
10,369,016 B2 8/2019 Lipsey et al.
10,369,024 B2 8/2019 Gill
10,398,576 B2 9/2019 Gill et al.
10,449,063 B2 10/2019 Gill
10,610,385 B2 4/2020 Meijer et al.
2001/0023058 A1 9/2001 Jung et al.
2002/0016631 A1 2/2002 Marchitto et al.
2002/0135241 A1 9/2002 Kobayashi et al.
2003/0036805 A1 2/2003 Senior
2003/0090115 A1 5/2003 Kim et al.
2004/0002672 A1 1/2004 Carlson
2004/0054423 A1 * 3/2004 Martin ...................... A61F 2/70 623/25
2004/0078299 A1 4/2004 Down-Logan et al.
2004/0103740 A1 6/2004 Townsend et al.
2004/0181289 A1 9/2004 Bedard et al.
2004/0182125 A1 9/2004 McLean
2005/0021154 A1 1/2005 Brimalm
2005/0021155 A1 1/2005 Brimalm
2005/0093997 A1 5/2005 Dalton et al.
2005/0101693 A1 5/2005 Arbogast et al.
2005/0102037 A1 5/2005 Matsuda
2005/0192677 A1 9/2005 Ragnarsdottir et al.
2006/0029909 A1 2/2006 Kaczkowski
2006/0054782 A1 3/2006 Olsen et al.
2006/0158146 A1 7/2006 Tadano
2006/0167564 A1 7/2006 Flaherty et al.
2006/0212129 A1 9/2006 Lake et al.
2006/0229755 A1 10/2006 Kuiken et al.
2006/0251408 A1 11/2006 Konno et al.
2007/0032884 A1 2/2007 Veatch
2007/0058860 A1 3/2007 Harville et al.
2007/0061111 A1 3/2007 Jung et al.
2007/0071314 A1 3/2007 Bhatti et al.
2007/0102228 A1 5/2007 Shiina et al.
2007/0137351 A1 6/2007 Schwendemann
2007/0230832 A1 10/2007 Usui et al.
2007/0260328 A1 11/2007 Bertels et al.
2007/0276303 A1 * 11/2007 Jenner, Jr. ............... A61F 2/586 602/21
2008/0058668 A1 3/2008 Seyed Momen et al.
2008/0097269 A1 * 4/2008 Weinberg .................. A61F 2/70 602/16
2008/0146981 A1 6/2008 Greenwald et al.
2008/0215162 A1 9/2008 Farnsworth et al.
2008/0260218 A1 10/2008 Smith et al.
2008/0262634 A1 10/2008 Puchhammer
2009/0145254 A1 6/2009 Hirabayashi et al.
2009/0213379 A1 8/2009 Carroll et al.
2010/0016990 A1 1/2010 Kurtz
2010/0036507 A1 * 2/2010 Gow ......................... A61F 2/68 623/64
2010/0116078 A1 * 5/2010 Kim ....................... H01R 35/04 74/490.02
2010/0274365 A1 * 10/2010 Evans ..................... A61F 2/585 623/57
2011/0048098 A1 * 3/2011 Rollins ................... B25F 5/005 72/453.15
2011/0203027 A1 8/2011 Flather et al.
2011/0237381 A1 9/2011 Puchhammer
2011/0257765 A1 10/2011 Evans et al.
2011/0264238 A1 10/2011 van der Merwe et al.
2011/0265597 A1 11/2011 Long
2011/0278061 A1 11/2011 Farnan
2012/0004884 A1 1/2012 Fillol et al.
2012/0014571 A1 1/2012 Wong et al.
2012/0061155 A1 3/2012 Berger et al.
2012/0099788 A1 4/2012 Bhatti et al.
2012/0109337 A1 5/2012 Schulz
2012/0204665 A1 8/2012 Baudasse
2012/0280812 A1 11/2012 Sheikman et al.
2012/0286629 A1 11/2012 Johnson et al.
2012/0303136 A1 * 11/2012 Macduff ................. A61F 2/586 623/63
2012/0330439 A1 12/2012 Goldfarb et al.
2013/0041476 A1 2/2013 Schulz
2013/0053984 A1 2/2013 Hunter et al.
2013/0076699 A1 3/2013 Spencer
2013/0144197 A1 6/2013 Ingimundarson et al.
2013/0175816 A1 7/2013 Kawasaki et al.
2013/0226315 A1 8/2013 Varley
2013/0253705 A1 9/2013 Goldfarb et al.
2013/0268090 A1 * 10/2013 Goldfarb ................... A61F 2/60 623/24
2013/0268094 A1 * 10/2013 Van Wiemeersch ...... A61F 4/00 623/57
2013/0310949 A1 * 11/2013 Goldfarb ................... A61F 2/70 623/27
2014/0060236 A1 * 3/2014 Watanabe ............ B25J 19/0075 74/490.06
2014/0148918 A1 5/2014 Pedersen et al.
2014/0148919 A1 5/2014 Pedersen et al.
2014/0236314 A1 8/2014 Van Wiemeersch
2014/0251056 A1 * 9/2014 Preuss ..................... B23P 11/00 74/490.05
2014/0277588 A1 9/2014 Patt et al.
2014/0324189 A1 10/2014 Gill et al.
2014/0371871 A1 12/2014 Farina et al.
2015/0112448 A1 4/2015 Scott et al.
2015/0142082 A1 5/2015 Simon et al.
2015/0183069 A1 * 7/2015 Lee ........................ B25J 9/0087 29/799
2015/0190245 A1 7/2015 McLeary et al.
2015/0216679 A1 * 8/2015 Lipsey .................... A61F 2/583 623/24
2015/0216681 A1 8/2015 Lipsey et al.
2015/0230941 A1 8/2015 Jury
2015/0351935 A1 12/2015 Donati et al.
2015/0360369 A1 * 12/2015 Ishikawa ................ B25J 9/1674 29/428
2015/0374515 A1 12/2015 Meijer et al.
2016/0089251 A1 3/2016 Mandl et al.
2016/0166409 A1 6/2016 Goldfarb et al.
2016/0250044 A1 9/2016 Iversen et al.
2016/0287422 A1 10/2016 Kelly et al.
2016/0296345 A1 10/2016 Deshpande et al.
2016/0367383 A1 12/2016 Sensinger et al.
2017/0049586 A1 2/2017 Gill et al.
2017/0168565 A1 6/2017 Cohen et al.

(56) References Cited

U.S. PATENT DOCUMENTS

| | | | | |
|---|---|---|---|---|
| 2017/0281368 | A1 | 10/2017 | Gill | |
| 2017/0340459 | A1 | 11/2017 | Mandelbaum | |
| 2018/0036145 | A1 | 2/2018 | Jury et al. | |
| 2018/0064563 | A1* | 3/2018 | Gill | A61F 2/68 |
| 2018/0071115 | A1 | 3/2018 | Lipsey et al. | |
| 2018/0098862 | A1 | 4/2018 | Kuiken et al. | |
| 2018/0116829 | A1 | 5/2018 | Gaston et al. | |
| 2018/0133032 | A1 | 5/2018 | Poirters | |
| 2018/0140441 | A1 | 5/2018 | Poirters | |
| 2018/0168830 | A1* | 6/2018 | Evans | A61F 2/70 |
| 2018/0207005 | A1 | 7/2018 | Chen et al. | |
| 2018/0221177 | A1 | 8/2018 | Kaltenbach et al. | |
| 2018/0256365 | A1 | 9/2018 | Bai | |
| 2018/0256366 | A1 | 9/2018 | Bai | |
| 2018/0263791 | A1 | 9/2018 | Bai | |
| 2018/0303633 | A1 | 10/2018 | Yi | |
| 2019/0091040 | A1* | 3/2019 | Gill | A61F 2/72 |
| 2019/0183661 | A1 | 6/2019 | Gill | |
| 2019/0209345 | A1* | 7/2019 | LaChappelle | A61F 2/72 |
| 2019/0216618 | A1 | 7/2019 | Gill | |
| 2019/0343660 | A1 | 11/2019 | Gill | |
| 2019/0380846 | A1 | 12/2019 | Lipsey et al. | |
| 2020/0054466 | A1 | 2/2020 | Gill et al. | |

FOREIGN PATENT DOCUMENTS

| | | |
|---|---|---|
| CN | 106994694 | 8/2017 |
| DE | 309 367 | 11/1918 |
| DE | 319 092 | 2/1920 |
| DE | 323 970 | 8/1920 |
| DE | 24 34 834 | 2/1976 |
| DE | 26 07 499 | 9/1977 |
| DE | 198 54 762 | 6/2000 |
| DE | 101 05 814 | 9/2002 |
| DE | 203 15 575 | 1/2004 |
| DE | 698 16 848 | 4/2004 |
| DE | 10 2012 009 699 | 11/2013 |
| DE | 10 2017 005 7 | 2/2020 |
| DE | 10 2017 005 761 | 2/2020 |
| DE | 10 2017 005 764 | 2/2020 |
| DE | 10 2017 005 765 | 2/2020 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 1 557 547 | 1/2011 |
| EP | 2 532 927 | 12/2012 |
| EP | 2 612 619 | 7/2013 |
| EP | 2 616 017 | 7/2013 |
| EP | 2 653 137 | 10/2013 |
| EP | 2 664 302 | 11/2013 |
| EP | 2 719 361 | 4/2014 |
| EP | 2 114 315 | 5/2016 |
| EP | 2 890 333 | 12/2016 |
| EP | 2 978 389 | 5/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| JP | 2018-167375 | 11/2018 |
| WO | WO 95/024875 | 9/1995 |
| WO | WO 96/023643 | 8/1996 |
| WO | WO 99/021517 | 5/1999 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2013/038143 | 3/2013 |
| WO | WO 2014/027897 | 2/2014 |
| WO | WO 2015/120076 | 8/2015 |
| WO | WO 2015/120083 | 8/2015 |
| WO | WO 2015/128604 | 9/2015 |
| WO | WO 2016/051138 | 4/2016 |
| WO | WO 2017/061879 | 4/2017 |
| WO | WO 2017/084637 | 5/2017 |
| WO | WO 2017/199127 | 11/2017 |
| WO | WO 2017/212128 | 12/2017 |
| WO | WO 2018/006722 | 1/2018 |
| WO | WO 2018/054945 | 3/2018 |
| WO | WO 2018/056799 | 3/2018 |
| WO | WO 2018/096188 | 5/2018 |
| WO | WO 2018/121983 | 7/2018 |
| WO | WO 2018/130428 | 7/2018 |
| WO | WO 2018/132711 | 7/2018 |
| WO | WO 2018/158554 | 9/2018 |
| WO | WO 2018/178420 | 10/2018 |
| WO | WO 2018/180782 | 10/2018 |
| WO | WO 2018/218129 | 11/2018 |
| WO | WO 2020/208557 | 10/2020 |
| WO | WO 2020/234777 | 11/2020 |

OTHER PUBLICATIONS

Albu-Schaffer et al., "Soft Robotics", IEEE Robotics & Automation Magazine, Sep. 2008, vol. 15, No. 3, pp. 20-30.

Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.

Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.

(56) References Cited

OTHER PUBLICATIONS

Belter et al., "Mechanical Design and Performance Specifications of Anthropomorphic Prosthetic Hands: A Review", JRRD, Jan. 2013, vol. 50, No. 5, pp. 599-618.
Biddiss et al., "Consumer Design Priorities for Upper Limb Prosthetics", Disability and Rehabilitation: Assistive Technology, Nov. 2007, vol. 2, No. 6, pp. 346-357.
Biddiss et al., "Upper Limb Prosthesis Use and Abandonment: A Survey of the Last 25 Years", Prosthetics and Orthotics International, Sep. 2007, vol. 31, No. 3, pp. 236-257.
Biddiss et al., "Upper-Limb Prosthetics: Critical Factors in Device Abandonment", American Journal of Physical Medicine & Rehabilitation, Dec. 2007, vol. 86, No. 12, pp. 977-987.
Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.
Childress et al., "Control of Limb Prostheses", American Academy of Orthopaedic Surgeons, Chapter 12, pp. 173-195, 2004.
Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.
Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.
Connolly, "Prosthetic Hands from Touch Bionics", Industrial Robot, Emerald Group Publishing Limited, 2008, vol. 35, No. 4, pp. 290-293.
Controzzi et al., "Miniaturized Non-Back-Drivable Mechanism for Robotic Applications", Mechanism and Machine Theory, Oct. 2010, vol. 45, No. 10, pp. 1395-1406.
Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.
"DC Circuit Theory", https://www.electronics-tutorials.ws/dccircuits/dcp_1.html, Date verified by the Wayback Machine Apr. 23, 2013, pp. 16.
Dechev et al., "Multiple Finger, Passive Adaptive Grasp Prosthetic Hand", Mechanism and Machine Theory, Oct. 1, 2001, vol. 36, No. 10, pp. 1157-1173.
Dellorto, Danielle, "Bionic Hands Controlled by iPhone App", CNN, Apr. 12, 2013, pp. 4 http://www.cnn.com/2013/04/12/health/bionic-hands.
"DuPont Engineering Design—The Review of DuPont Engineering Polymers in Action", http://www.engpolymer.co.kr/x_data/magazine/engdesign07_2e.pdf, Feb. 2007, pp. 16.
Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.
Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaine et al., "Upper Limb Traumatic Amputees. Review of Prosthetic Use", The Journal of Hand Surgery, Feb. 1997, vol. 22B, No. 1, pp. 73-76.
Grip Chips™, Datasheet, May 15, 2014, Issue 1, http://touchbionics.com/sites/defalut/files/Grip%20Chip%20datasheet%20May%202014.pdf, pp. 1.
Heckathorne, Craig W., "Components for Electric-Powered Systems", American Academy of Orthopaedic Surgeons, Chapter 11, pp. 145-171, 2004.
Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.
Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.
International Preliminary Report on Patentability and Written Opinion in Application No. PCT/GB2015/050337, dated Sep. 9, 2016.
Jebsen et al., "An Objective and Standardized Test of Hand Function", Archives of Physical Medicine and Rehabilitation, Jun. 1969, vol. 50, No. 6, pp. 311-319.
Johannes et al., "An Overview of the Developmental Process for the Modular Prosthetic Limb," John Hopkins APL Technical Digest, 2011, vol. 30, No. 3, pp. 207-216.
Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Kyberd et al., "Two-Degree-of-Freedom Powered Prosthetic Wrist", Journal of Rehabilitation Research & Development, 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.
Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Majd et al., "A Continuous Friction Model for Servo Systems with Stiction", in Proceedings of the IEEE Conference on Control Applications, 1995, pp. 296-301.
Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
Maxon Precision Motors, Inc., "Maxon Flat Motor: EX 10 flat 10 mm, brushless, 0.25 Watt", Specification, May 2011, p. 181.
Maxon Precision Motors, Inc., "Maxon EC Motor: EC10 10 mm, brushless, 8 Watt", Specification, May 2011, p. 140.
Miller et al., "Summary and Recommendations of the Academy's State of the Science Conference on Upper Limb Prosthetic Outcome Measures", Journal of Prosthetics Orthotics, 2009, vol. 21, pp. 83-89.
Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.
Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.
Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.
Osborn et al., "Utilizing Tactile Feedback for Biomimetic Grasping Control in Upper Limb Prostheses". Department of Biomedical Engineering, Johns Hopkins University, Baltimore, USA, 2013, pp. 4.

(56) References Cited

OTHER PUBLICATIONS

Pedrocchi et al., "MUNDUS Project: Multimodal Neuroprosthesis for Daily Upper Limb Support", Journal of Neuroengineering and Rehabilitation, 2013, vol. 10, No. 66, pp. 20. http://www.ineuroengrehab.com/content/10/1/66.
Pinzur et al., "Functional Outcome Following Traumatic Upper Limb Amputation and Prosthetic Limb Fitting", J. Hand Surgery, Amer. vol. 1994. vol. 19, pp. 836-839.
Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.
Raspopovic et al., "Restoring Natural Sensory Feedback in Real-Time Bidirectional Hand Prostheses", Science Translational Medicine, Feb. 5, 2014, vol. 6, No. 222, pp. 1-10.
Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.
Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.
Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.
Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.
Sensinger, "Efficiency of High-Sensitivity Gear Trains, such as Cycloid Drives", Journal of Mechanical Design, Jul. 2013, vol. 135, No. 7, pp. 071006-1-071006-9.
Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.
Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.
Stix, Gary, "Phantom Touch: Imbuing a Prosthesis with Manual Dexterity", Scientific American, Oct. 1998, pp. 41 & 44.
Sutton et al., "Towards a Universal Coupler Design for Modern Powered Prostheses", MEC 11 Raising the Standard, Proceedings of the 2011 MyoElectric Controls/Powered Prosthetics Symposium Frederiction, New Brunswick, Canada, Aug. 14-19, 2011, pp. 5.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", The Journal of Hand Surgery, European Volume, Aug. 2008, vol. 33, No. 4, pp. 519-525.
Toledo et al., "A Comparison of Direct and Pattern Recognition Control for a Two Degree-of-Freedom Above Elbow Virtual Prosthesis", in Proceedings 34th Annual International Conference of the IEEE EMBS, 2012, pp. 4332-4335.
"Touch Bionics Grip Chips Let Hand Prostheses Think for Themselves", May 15, 2014, www.medgadget.com/2014/05/touch-bionics-grip-chips-let-hand-prosthesis-think-for-themselves.html, pp. 2.
Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.
Vilarino, Martin, "A Novel Wireless Controller for Switching among Modes for an Upper-Limb Prosthesis", The Academy TODAY, Jan. 2014, vol. 10, No. 1, pp. A-12 to A-15.
Weir et al., "Design of Artificial Arms and Hands for Prosthetic Applications", Biomedical Engineering and Design Handbook, 2009, vol. 2, pp. 537-598.
Wettels et al., "Grip Control Using Biomimetic Tactile Sensing Systems", IEEE/ASME Transactions on Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.
"Supro Wrist", Touch Bionics, as archived Sep. 28, 2016 in 3 pages from https://web.archive.org/web/20160928141440/http://www.touchbionics.com/products/supro-wrist.
9 Worm Gear Pair, KHK Technical Information, Date Unavailable, pp. 291-299.
AMA, Excerpts from American Medical Association, Guides to the Evaluation of Permanent Impairment (5th ed. 2000), pp. 432-453.
Baek et al., "Design and Control of a Robotic Finger for Prosthetic Hands", Proceedings of the 1999 IEEE International Conference on Intelligent Robots and Systems, pp. 113-117.
Bretthauer et al., "A New Adaptive Hand Prosthesis", Handchirurgie Mikrochirurgie Plastische Chirurgie, Feb. 2008, pp. 40-45.
Butterfaβ et al., "DLR-Hand II: Next Generation of a Dextrous Robot Hand", IEEE International Conference on Robotics and Automation, Seoul, Korea, May 21-26, 2001, vol. 1, pp. 109-114.
Cotton et al., "Control Strategies for a Multiple Degree of Freedom Prosthetic Hand", Measurement + Control, Feb. 2007, vol. 40, No. 1, pp. 24-27.
Edsinger-Gonzales, Aaron, "Design of a Compliant and Force Sensing Hand for a Humanoid Robot", 2005, pp. 5.
Fildes, Jonathan, "Bionic Hand Wins Top Tech Prize", BBC News, Jun. 9, 2008, http://news.bbc.co.uk/2/hi/science/nature/7443866.stm, pp. 3.
Gaiser et al., "A New Anthropomorphic Robotic Hand", 2008 8th IEEE-RAS International Conference on Humanoid Robots, Dec. 1-3rd, 2008, Daejeon, Korea, pp. 418-422.
"iLimb Bionic Hand Now Ready for Market", Technovelgy.com, www.technovelgy.com/ct/Science-Fiction-News.asp?NewsNum=1125, as printed Jul. 6, 2020 in 3 pages.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
"Motor Technology—Girard Gearboxes Low Backlash Principle Explained", Motor Technology, https://www.motec.co.uk/tip-gearbox_principle.htm as printed May 23, 2012 in 3 pages.

(56) References Cited

OTHER PUBLICATIONS

Poppe, Zytel HTN Provides a Helping Hand, DuPont Engineering Design 8 (2007), pp. 3.
Puig et al., "A Methodology for the Design of Robotic Hands with Multiple Fingers", International Journal of Advanced Robotic Systems, 2008, vol. 5, No. 2, pp. 177-184.
Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopadie-Technik 08/06, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365. [Uploaded in 3 Parts].
Ward, Derek Kempton, "Design of a Two Degree of Freedom Robotic Finger", Sep. 1996, pp. 155.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.

* cited by examiner

PROSTHETIC DIGIT FOR USE WITH TOUCHSCREEN DEVICES

FIELD OF THE INVENTION

The present invention is directed to the field of prosthetics and orthotics, and in particular a hand prosthetic. More specifically the present invention is directed to digits used on prosthetic hands, and to a digit which will allow the wearer to operate a touchscreen device with such a digit.

BACKGROUND OF THE INVENTION

Many amputees and partial amputees now wear prosthetic hands incorporating powered and/or non-powered digits. As mobile telephone and device technology has developed in recent years, many of those persons now own a mobile telephone, tablet or other device which has a touchscreen. The touchscreens in the majority of these devices detect a user's input using sensors and circuitry to monitor changes in a particular state of the screen. Many of these devices employ capacitive touchscreens which use a layer of capacitive material to hold an electrical charge, and when the user's finger touches the screen the capacitance at the point of contact changes, thereby indicating at which point the user is touching the screen.

The digits of hand prosthetics are typically formed from stainless steel or a similar metal and are usually covered by some form of protective and/or aesthetic cover formed from an elastomer. The elastomer layer may or may not be covered in certain areas by polyurethane or the like so as to aid donning and removal of the cover. The presence of such covers presents a problem to a prosthetic wearer who wishes to operate the aforementioned touchscreens, as the cover interferes with the ability of the user to change the capacitance when touching the touchscreen. Prosthetic wearers who still have one hand can choose to operate the device with that hand, but this can be inconvenient and is obviously not an option for those who have lost both hands.

It has been established that simply removing the cover from the digit and using the metal digit to touch the screen does not change the capacitance as needed. One solution which has been proposed has been to provide a metal pad or dome at the tip of the digit. However, it has been found that the success of this arrangement is dependent on the specific shape of the contact surface on the digit and also this very often leads to scratching and cracking of the relatively delicate screen after frequent sweeping and tapping motions by the metal pad. Another proposal has been to provide conductive threads in the digit covers, with the threads running along the length of the cover from the tip. However it has been found that repeated folding and extending motions of the digits can cause these threads to wear and break relatively quickly, thereby preventing the required change in capacitance. A further solution has been to connect the digit tip to an external conductive wire. However, running a conductive wire down the entire length of the digit increases the likelihood of the wire fouling upon another component or object or accelerating fatigue in the wire as it is stretched every time the digit is closed, with the result being an increased likelihood of damage to, or failure of, the conductive wire.

It is an aim of the present invention to obviate or mitigate one or more of these disadvantages.

SUMMARY OF THE INVENTION

According to a first aspect of the invention there is provided a digit for a prosthetic hand, the digit comprising:

a base member attachable to the hand; and at least one digit member pivotably connected to the base member;

wherein the at least one digit member has a digit tip remote from the base member, and the digit member is at least partially covered with at least one conductive substance which defines a conductive path which leads from the digit tip towards the base member.

The digit may further comprise a cover adapted to fit over at least the digit tip, the cover having a cover tip which lies over the digit tip when the cover is in place, wherein the cover tip includes at least one aperture extending through the cover, and the at least one conductive substance is provided on an exterior of the cover tip and within the at least one aperture such that it defines part of the conductive path from the exterior of the cover tip to the digit tip.

The at least one conductive substance may be selected from the group comprising: a conductive adhesive, a conductive paint and a conductive coating.

Alternatively, the digit tip may be at least partially covered with a first conductive substance, and an adjacent portion of the at least one digit member is at least partially covered with a second conductive substance, the first and second conductive substances defining the conductive path.

The first conductive substance may be a conductive adhesive, and the second conductive substance may be a conductive paint.

The digit may further comprise:

a first digit member pivotably connected to the base member;

a second digit member pivotably connected to the first digit member, the second digit member including the digit tip at a remote end thereof; and a biasing member having a first end connected to the first digit member and a second end connected to the second digit member, the biasing member biasing the second digit member towards substantial alignment with the first digit member;

wherein the at least one conductive substance is provided on the second digit member, and the biasing member extends the conductive path from the second digit member to the first digit member.

The digit may be a powered digit and further comprise a motor contained within a motor casing, and a conductive wire having a first end connected to the first end of the biasing member, and a second end connected to the motor casing.

According to a second aspect of the invention there is provided a method of manufacturing a digit for a prosthetic hand, the method comprising the steps of:

pivotably connecting at least one digit member to a base member which is attachable to the hand, the digit member having a digit tip which is remote from the base member; and at least partially covering the at least one digit member with at least one conductive substance which defines a conductive path which leads from the digit tip towards the base member.

The method may further comprise the steps of:

providing a cover to cover at least the digit tip, the cover having a cover tip which lies over the digit tip when in use;

forming at least one aperture in the cover tip such that the aperture extends through the cover;

inserting a portion of the at least one conductive substance into the at least one aperture such that the conductive substance is provided on an exterior of the cover tip and within the at least one aperture; and fitting the cover over the digit tip, such that the at least one conductive substance defines part of the conductive path from the exterior of the cover tip to the digit tip.

The at least one conductive substance may be selected from the group comprising: a conductive adhesive, a conductive paint, a conductive coating and a conductive film.

Alternatively, the method may further comprise the steps of:

at least partially covering the digit tip with a first conductive substance; and at least partially covering an adjacent portion of the at least one digit member with a second conductive substance;

wherein the first and second conductive substances define the conductive path.

The first conductive substance may be a conductive adhesive, and the second conductive substance may be a conductive paint.

The method may further comprise the steps of:

forming first and second digit members, wherein the second digit member includes the digit tip at a remote end thereof and the at least one conductive substance is provided on the second digit member;

pivotably connecting the first digit member to the base member;

pivotably connecting the second digit member to the first digit member; and connecting a first end of a biasing member to the first digit member and a second end of the biasing member to the second digit member, such that the biasing member biases the second digit member towards substantial alignment with the first digit member, and the biasing member extends the conductive path from the second digit member to the first digit member.

The method may further comprise the steps of:

providing the digit with a motor contained within a motor casing;

connecting a first end of a conductive wire to the first end of the biasing member; and connecting the second end of the conductive wire to the motor casing.

BRIEF DESCRIPTION OF THE DRAWINGS

A preferred embodiment of the present invention will now be described, by way of example only, with reference to the following drawings.

DETAILED DESCRIPTION OF THE DRAWINGS

Figure 1:
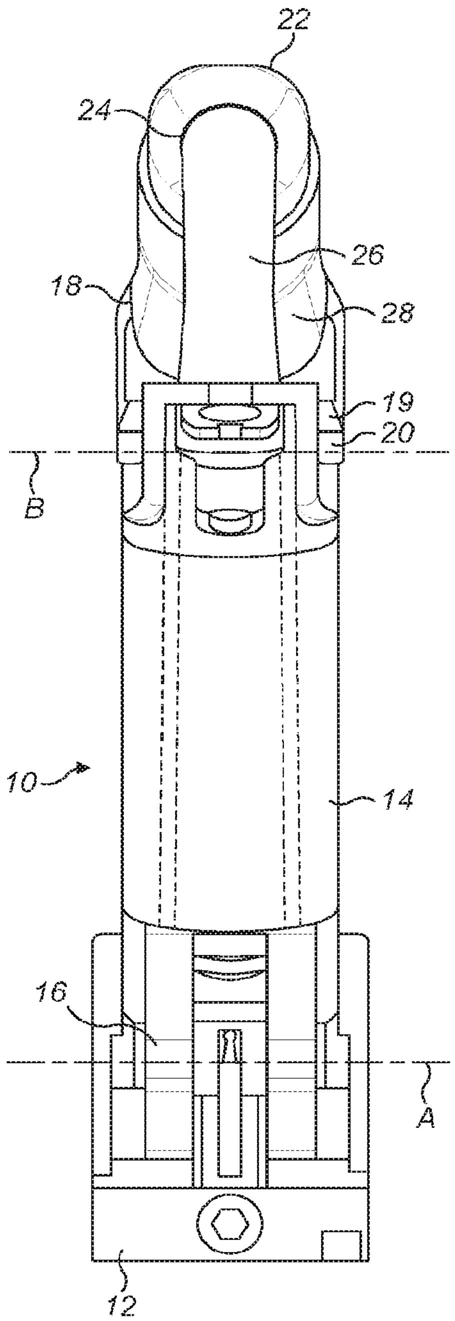
FIG. 1 is a front view of a digit for a prosthetic hand.

FIG. 1 shows a front view of a digit 10 for use in a prosthetic hand of an amputee or partial amputee. The present invention may be applied to both powered and non-powered digits, but for the purposes of this example the digit is powered.

The digit may be formed from aluminium, stainless steel or another ferrous metal which allows conduction. Alternatively, the digit may be formed from a plastics material. The digit 10 comprises a base or support member 12 which allows the digit 10 to be secured to a hand chassis or mount (not shown) which is attached to the hand or residual stump of the wearer in a known manner. A first digit member 14 is connected to the base member 12 about a first, or proximal, pivot rod 16 which allows the first digit member 14 to pivot about a rotational axis A of the first rod 16 relative to the base member 12. A second digit member 18 is connected to a distal end of the first digit member 14 about a second, or distal, pivot rod 20 which allows the second digit member 18 to pivot about a rotational axis B of the second rod 20 relative to the first digit member 14. The second digit member 18 includes a tip 22 at the end of the second digit member 18 which is remote from the second rod 20. The tip 22 may include a flattened surface 24 which is intended to replicate the pad of a human fingertip. An electrically conductive paint or coating 26 is applied to the tip 22 and front face 28 (that is, the face of the second digit member 18 facing the viewer in FIG. 1) of the second digit member 18 so as to create a conductive track or path from the tip 22 to a proximal end 19 of the second digit member 18. A non-limiting example of a paint or coating suitable for this purpose is "Silver Conductive Paint" sold by RS Components Limited of Corby, United Kingdom. This paint has a silver content of 35-65%.

Figure 2:
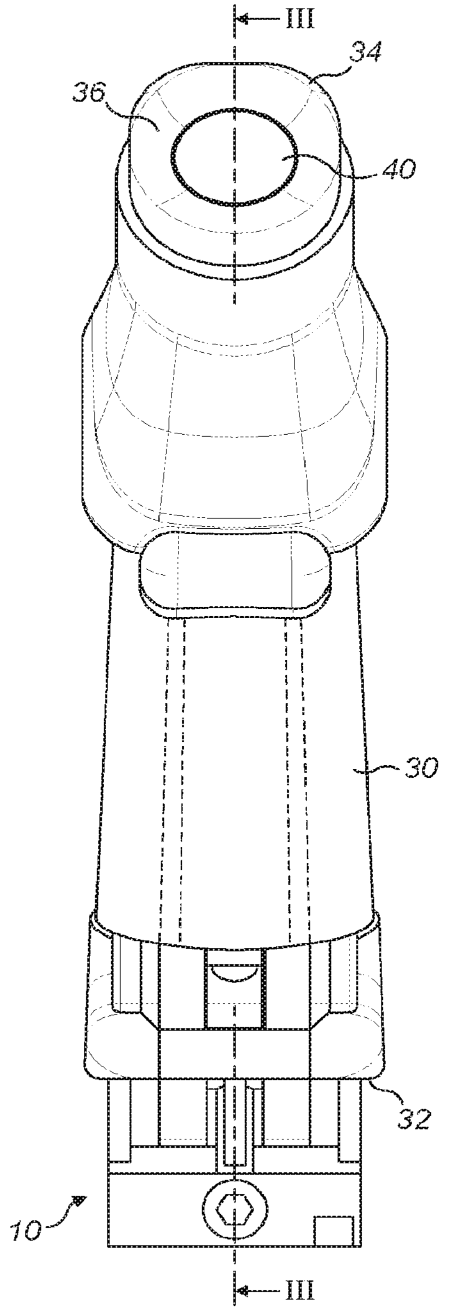
FIG. 2 is a front view of the digit shown in FIG. 1 with a protective cover over the digit.
Figure 3:
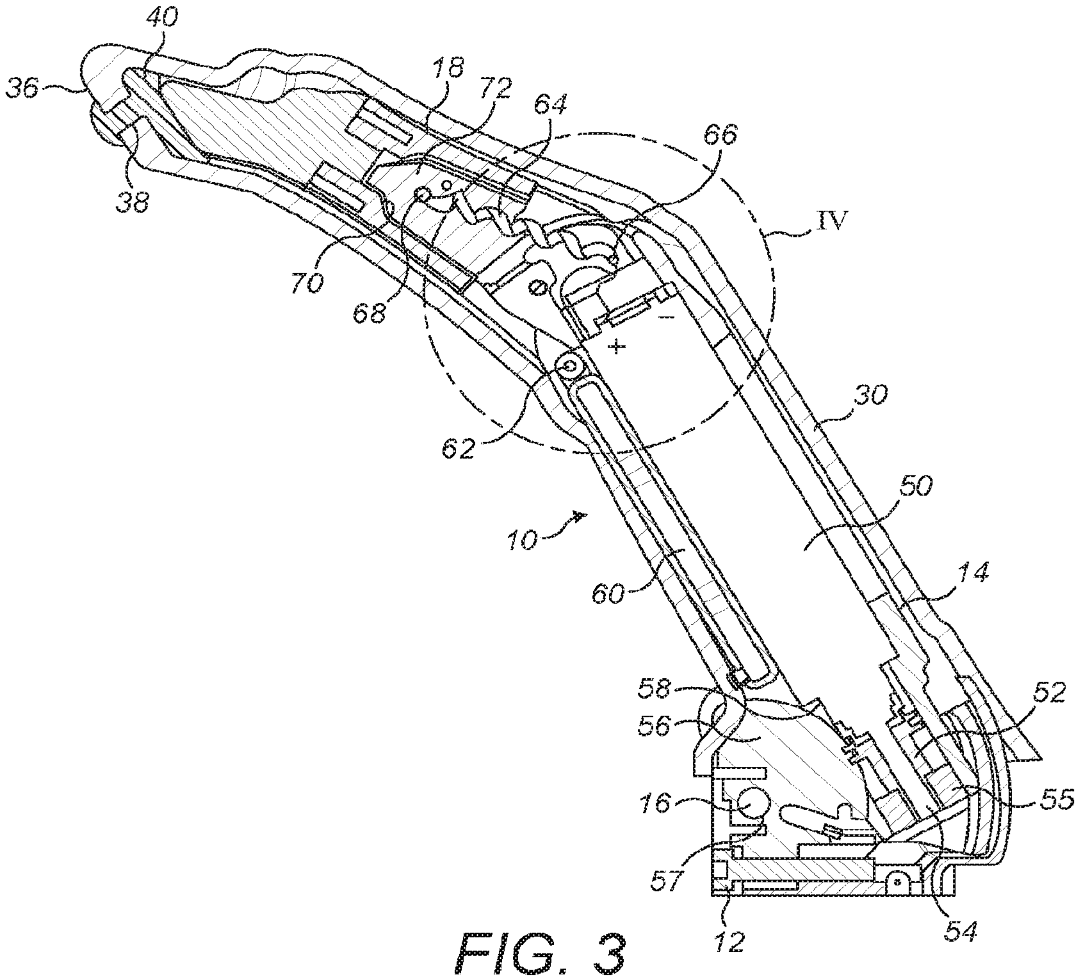
FIG. 3 is a section view of the digit along the line III-Ill shown in FIG. 2.

FIG. 2 shows the same view of the digit 10 as in FIG. 1, but the digit 10 has now been covered by a cover 30. The cover 30 has a proximal end 32 which is open and a remote end 34 which is closed. The cover 30 is preferably formed as a single piece from an elastomer, and the internal surface of the cover may be at least partly coated in polyurethane to allow the cover 30 to more easily slip on and off the digit 10. The remote end 34 of the cover 30 has a tip 36 which corresponds with the digit tip 22 beneath. The tip 36 has at least one aperture 38 which extends all the way through the cover 30. A conductive adhesive 40 is injected through the aperture(s) 38 so that a portion of the adhesive adheres to the internal surface of the cover 30 adjacent the tip 36. As best shown in FIG. 3, the adhesive 40 extends from the internal surface of the cover 30 outwards through the aperture(s) 38 and a portion is also left upon the external surface of the cover 30 at the tip 36. A non-limiting example of a conductive adhesive suitable for this purpose is "Kembond SNG-RTV" sold by Kemtron Limited of Braintree, United Kingdom. This particular product is an electrically conductive adhesive comprising nickel graphite particles within a silicon resin.

FIG. 3 is a sectional view of the digit 10 and cover 30 taken along the line shown in FIG. 2. This view shows more details of the operating components of the digit 10 as well as the conductive path from the tip of the cover 30. Located within the interior of the first digit member 14 is a motor 50, which is operable to drive a worm gear 52 located on a drive shaft 54 extending from the motor 50. A bearing SS is positioned at the distal end of the drive shaft 54. A worm gear wheel 56 is fixedly mounted on the base member 12, and the digit 10 extends generally tangentially with respect to the worm gear wheel 56 and is mounted for rotation about the worm gear wheel 56. The first digit member 14 is connected to the worm gear wheel 56 via the pivot rod 16 which passes through a circular aperture 57 in the worm gear wheel 56, thereby forming a first joint about rotational axis A. The worm gear 52 is in engagement with the worm gear wheel 56 such that, when the motor 50 is operated in use of the digit 10, the first digit member 14 rotates about the worm gear wheel 56.

It can also be seen in FIG. 3 that the first digit member 14 is coupled to the second digit member 18 by a coupling mechanism, which is arranged such that when the first digit member 14 rotates about the worm gear wheel 56, the second digit member 18 pivots with respect to the first digit member 14. The coupling mechanism includes one or more cables 60, which are connected between a coupling pin 62 on the second digit member 18 and the worm gear wheel 56 or base member 12. As a result, when the first digit member 14 pivots with respect to the worm gear wheel 56, the one or more cables 60 pull on the coupling pin 62 and move the second digit member 18 towards the worm gear wheel 56, i.e. a movement which mimics the closing of a finger of a human hand.

A biasing member 64 has a first end connected to the first digit member 14 by a first biasing pin 66, and a second end connected to the second digit member 18 by a second biasing pin 68. The biasing member 64 consequently spans the joint between the first and second digit members 14,18 and is offset from a longitudinal axis of the digit 10 such that it biases the second digit member 18 into alignment with the first digit member 14, i.e. towards an extended position away from the aforementioned closed position.

The biasing member 64 could be connected into the first and second digit members 14,18 in a number of ways. In the illustrated embodiment the proximal end of the second digit member 18 contains a hollow chamber 70, whose internal surface is coated with the same conductive paint or coating as the front face 28 of the second digit member 18. The first end of the biasing member 64 is connected into a plastic insert 72 by the first biasing pin 66. The external surface of the insert 72 is also coasted with the conductive paint or coating. The insert 72 is threaded or otherwise fixed into the chamber 70 to provide the connection between the first end of the biasing member 64 and the second digit member 18, as well as a conductive path from the second digit member 18 to the biasing member 64.

Figure 4:
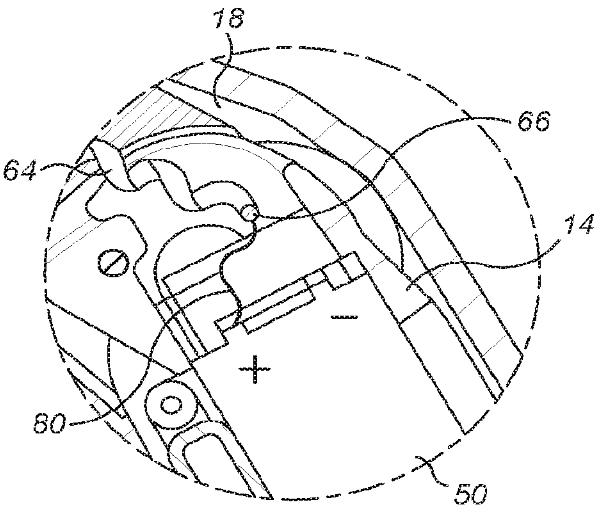
FIG. 4 is a detail view of the section marked IV in FIG. 3.

As can be seen in the detail view of FIG. 4, the first biasing pin 66 is connected to the positive terminal of the motor 50 by a wire connector 80. The wire connector 80 has a degree of slack so as to allow the second digit member 18 to pivot relative to the first digit member 14 without the wire connector 80 being pulled taut or being strained in any way. In this way the wire connector 80 continues the conductive path from the first end of the biasing member 64 to a casing 58 of the motor 50 or alternatively to the support member 12.

The first digit member 14 may include at least one electrical contact member (not shown) and the worm gear wheel 56 may include at least one electrical contact surface (not shown). The electrical contact member and the electrical contact surface are used to supply electrical power to the motor 50 and may also act as part of the conductive path. The electrical contact member is connected to the terminal inputs of the motor 50 via electrical wires (not shown). The electrical contact surface is connected to an electrical power source which is located in the main body of the prosthesis (not shown). The electrical contact member and the electrical contact surface are arranged to slidably contact one another as the first digit member 14 rotates about the worm gear wheel 56. The electrical contact member(s) may comprise, for example, pin members, brushes or sprung contacts.

As described above, the electrical contact members and the electrical contact surfaces are used to supply electrical power to the motor 50. The electrical contact surfaces may provide AC or DC electrical power to the motor 50 via the electrical contact members.

INDUSTRIAL APPLICABILITY

The manner in which the digit operates a touchscreen device will now be described. The hand prosthesis of which the digit 10 forms part will comprise an electronic device (not shown), which is configured to control the operation of the motor 50. The electronic device may be located within the main body of the prosthesis.

The motor 50 is operable via one or more switches not shown). The switches may be actuated by residual movement, or wrist and/or shoulder movement of the wearer of the hand prosthesis, or the like. Alternatively, or additionally, the motor 50 may be operable via signals derived from the activity of, or from, electromyographic (EMG) activity of residual muscle actions of the wearer, pressure sensitive resistors on the wearer, signals derived from one or more neural implants in the wearer, EMG activity from reinnervated muscles, muscles of the feet and/or chest, or the like. The electronic device is configured to process the actuation signals from the wearer to operate the motor 50.

In use the wearer provides a movement signal, for example, an EMG signal, to operate the motor 50. When the motor 50 receives the signal, via the electronic device, the drive shaft. 54 is rotated in a chosen direction. This causes the worm gear 52 to rotate and rotate the first digit member 14 about the worm gear wheel 56. Depending on the EMG signal and hence the direction of rotation of the drive shaft 54, the first digit member 14 rotates about the worm gear wheel 56 with both the first digit member and second digit member 18 closing in a hand grasping action, or the first digit member and second digit member opening in a hand extension action.

When the wearer wishes to operate a touchscreen device, they may choose to extend the digit 10 into a “pointing” position, or to the slightly bent configuration shown in FIG. 3. In order to operate the screen of the device, the tip 36 of the cover 30 is brought into contact with the desired area of the screen. In doing so, the portion of the conductive adhesive 40 left upon the external surface of the tip 36 comes into contact with the screen. This causes a change in capacitance to be registered by the capacitive resistance screen of the device due to the conductive path which passes through the aperture 38 in the cover along the adhesive 40. Once inside the cover 30, the path passes from the adhesive 40 to the conductive paint 26 which runs from the tip 22 of the second digit member 18 down the front face 28 of the second digit member 18.

As best seen in FIG. 3, the conductive paint 26 extends to the proximal end 19 of the second digit member 18 and then internally to the chamber 70 and plastic insert 72. As the facing surfaces of both the chamber 70 and insert 72 are also coated with the paint 26, the conductive path extends from the exterior of the second digit member 18 to the insert 72. From there, it runs onto the second biasing pin 68 and from the second digit member 18 to the first digit member 14 via the biasing member 64. The path then passes from the biasing member 64 to the wire connector 80 via the first biasing pin 66. The path then extends to the outer casing of the motor 50.

The present invention provides a digit for a prosthetic hand which means a wearer who still has one hand does not need to use their remaining hand to operate a touchscreen device. It also provides a more consistent contact and change in capacitance than previous proposals which rely upon a metal pad or dome at the tip of the digit. Providing a conductive substance on the elastomeric cover also avoids scratching and cracking of the touchscreen compared with such metal contact pads. The present invention also provides a consistent conductive path through the digit without any likelihood of the path being broken or intermittent due to repeated movements of the first and second digit members or due to exposed conductive wires which may be fouled or damaged during use of the digit/prosthesis.

Whilst the preferred digit described above is formed from a base member and first and second digit members, the digit of the present invention may be formed from a single digit member which is pivotably connected to a base member. In such a case the digit tip and its optional cover would be at the remote end of the single digit member from the base member.

Whilst it may be preferred to cover the digit, or at least the tip thereof, with a cover to protect against damage and ingress of dirt and other undesired substances, the cover is not an essential component of the present invention. In the absence of a cover, the first conductive substance may be applied to the digit tip directly along with the second conductive substance.

When a cover is employed it may have a plurality of apertures extending through the cover rather than the single aperture shown in the illustrated embodiment. As in the illustrated embodiment conductive adhesive or another conductive substance is injected through each aperture so that adhesive adheres to the internal surface of the cover adjacent the tip. The adhesive extends from the internal surface of the cover outwards through the apertures and a portion is also left upon the external surface of the cover at the tip.

Whilst the first conductive substance is a conductive adhesive in the preferred embodiment, it may alternatively be a conductive paint, a conductive coating or a conductive film. Similarly, whilst the second conductive substance is a conductive paint in the preferred embodiment, it may alternatively be a conductive adhesive, a conductive coating or a conductive film. Whilst the first and second substances are preferably different substances, they may alternatively be the same substance. In the case of a conductive film, the film may incorporate a length of a conductor so as to form a conductive track or path, or alternatively the conductor may be sandwiched between two layers of film.

Whilst the conductive path of the preferred example of the digit described herein is defined by applying the conductive substance to a limited region of the or each digit member, the entire digit member(s) may be covered with the conductive substance such that the conductive path from the digit tip is not limited to a single track of the conductive substance. In this instance the entire digit member(s) would act as the conductive path.

As stated above, the present invention encompasses non-powered digits as well as the powered digit of the preferred embodiment. In the case of a non-powered digit the conductive path defined by the conductive substance(s) may be extended by additional conductive substance(s) or a connector wire.

These and other modifications and improvements may be incorporated without departing from the scope of the present invention.

The invention claimed is:

1. A method of manufacturing a digit for a prosthetic hand, the method comprising the steps of:

pivotably connecting at least one digit member to a base member which is attachable to the prosthetic hand, the digit member having a digit tip which is remote from the base member;

at least partially covering the at least one digit member with at least one conductive substance which defines a conductive path which leads from the digit tip towards the base member;

providing a cover to cover at least the digit tip, the cover having a cover tip which lies over the digit tip when in use;

forming at least one aperture in the cover tip such that the aperture extends through the cover;

inserting a portion of the at least one conductive substance into the at least one aperture such that the conductive substance is provided on an exterior of the cover tip and within the at least one aperture; and fitting the cover over the digit tip, such that the at least one conductive substance defines part of the conductive path from the exterior of the cover tip to the digit tip.

2. The method of claim 1, wherein the at least one conductive substance is selected from the group comprising: a conductive adhesive, a conductive paint, a conductive coating and a conductive film.

3. The method of claim 1, further comprising the steps of:

at least partially covering the digit tip with a first conductive substance of the at least one conductive substance; and at least partially covering an adjacent portion of the at least one digit member with a second conductive substance of the at least one conductive substance, wherein the first and second conductive substances define the conductive path.

4. The method of claim 3, wherein the first conductive substance is a conductive adhesive, and the second conductive substance is a conductive paint.

5. The method of claim 1, further comprising the steps of:

forming first and second digit members of the at least one digit member, wherein the second digit member includes the digit tip at a remote end thereof and the at least one conductive substance is provided on the second digit member;

pivotably connecting the first digit member to the base member;

pivotably connecting the second digit member to the first digit member; and connecting a first end of a biasing member to the first digit member and a second end of the biasing member to the second digit member, such that the biasing member biases the second digit member towards substantial alignment with the first digit member, and the biasing member extends the conductive path from the second digit member to the first digit member.

6. The method of claim 5, further comprising the steps of:

providing the digit with a motor contained within a motor casing;

connecting a first end of a conductive wire to the first end of the biasing member; and connecting a second end of the conductive wire to the motor casing.

7. A method of manufacturing a digit for a prosthetic hand, the method comprising the steps of:

pivotably connecting at least one digit member to a base member which is attachable to the prosthetic hand, the digit member having a digit tip which is remote from the base member;

at least partially covering the at least one digit member with at least one conductive substance which defines a conductive path which leads from the digit tip towards the base member;

forming first and second digit members of the at least one digit member, wherein the second digit member includes the digit tip at a remote end thereof and the at least one conductive substance is provided on the second digit member;

pivotably connecting the first digit member to the base member;

pivotably connecting the second digit member to the first digit member; and connecting a first end of a biasing member to the first digit member and a second end of the biasing member to the second digit member, such that the biasing member biases the second digit member towards substantial alignment with the first digit member, and the biasing member extends the conductive path from the second digit member to the first digit member.

8. The method of claim 7, further comprising the steps of:

providing a cover to cover at least the digit tip, the cover having a cover tip which lies over the digit tip when in use;

forming at least one aperture in the cover tip such that the aperture extends through the cover;

inserting a portion of the at least one conductive substance into the at least one aperture such that the conductive substance is provided on an exterior of the cover tip and within the at least one aperture; and fitting the cover over the digit tip, such that the at least one conductive substance defines part of the conductive path from the exterior of the cover tip to the digit tip.

9. The method of claim 7, wherein the at least one conductive substance is selected from the group comprising: a conductive adhesive, a conductive paint, a conductive coating and a conductive film.

10. The method of claim 7, further comprising the steps of:

at least partially covering the digit tip with a first conductive substance of the at least one conductive substance; and at least partially covering an adjacent portion of the at least one digit member with a second conductive substance of the at least one conductive substance, wherein the first and second conductive substances define the conductive path.

11. The method of claim 10, wherein the first conductive substance is a conductive adhesive, and the second conductive substance is a conductive paint.

12. The method of claim 7, further comprising the steps of:

providing the digit with a motor contained within a motor casing;

connecting a first end of a conductive wire to the first end of the biasing member; and connecting a second end of the conductive wire to the motor casing.

13. A method of manufacturing a digit for a prosthetic hand, the method comprising the steps of:

pivotably connecting at least one digit member to a base member which is attachable to the prosthetic hand, the digit member having a digit tip which is remote from the base member;

at least partially covering the at least one digit member with at least one conductive substance which defines a conductive path which leads from the digit tip towards the base member;

providing a cover to cover at least the digit tip, the cover having a cover tip which lies over the digit tip when in use; and fitting the cover over the digit tip, such that the at least one conductive substance defines part of the conductive path from an exterior of the cover tip to the digit tip.

14. The method of claim 13, wherein the at least one conductive substance is selected from the group comprising: a conductive adhesive, a conductive paint, a conductive coating and a conductive film.

15. The method of claim 13, further comprising the steps of:

at least partially covering the digit tip with a first conductive substance of the at least one conductive substance; and at least partially covering an adjacent portion of the at least one digit member with a second conductive substance of the at least one conductive substance, wherein the first and second conductive substances define the conductive path.

16. The method of claim 15, wherein the first conductive substance is a conductive adhesive, and the second conductive substance is a conductive paint.

17. The method of claim 13, further comprising the steps of:

forming first and second digit members of the at least one digit member, wherein the second digit member includes the digit tip at a remote end thereof and the at least one conductive substance is provided on the second digit member;

pivotably connecting the first digit member to the base member;

pivotably connecting the second digit member to the first digit member; and connecting a first end of a biasing member to the first digit member and a second end of the biasing member to the second digit member, such that the biasing member biases the second digit member towards substantial alignment with the first digit member, and the biasing member extends the conductive path from the second digit member to the first digit member.

18. The method of claim 17, further comprising the steps of:

providing the digit with a motor contained within a motor casing;

connecting a first end of a conductive wire to the first end of the biasing member; and connecting a second end of the conductive wire to the motor casing.

* * * * *